Figure 1:
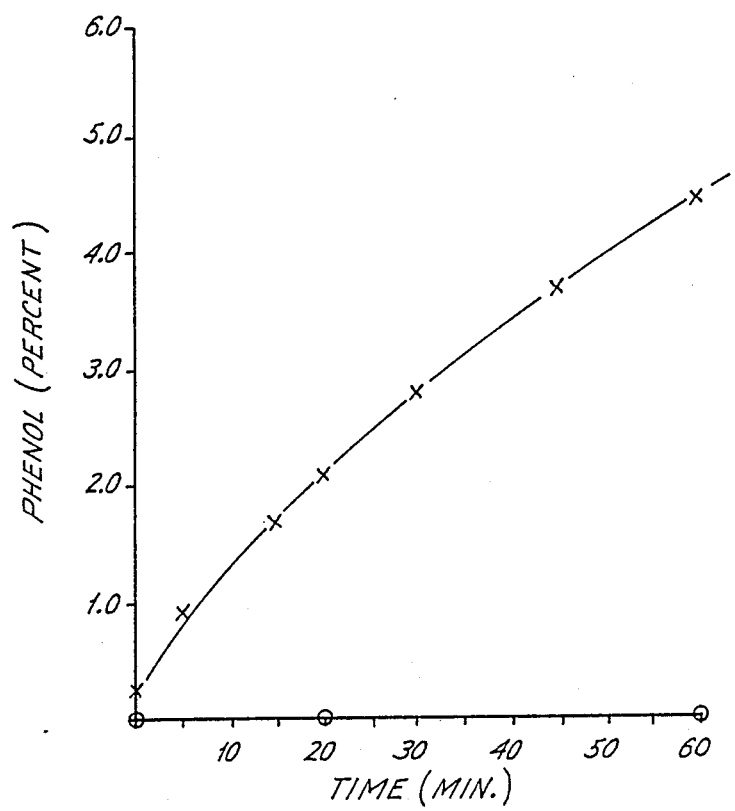

United States Patent [19]

Knifton

[11] Patent Number: 4,898,987
[45] Date of Patent: Feb. 6, 1990

[54] METHOD FOR PRODUCTION OF PHENOL/ACETONE FROM CUMENE HYDROPEROXIDE

[75] Inventor: John F. Knifton, Austin, Tex.

[73] Assignee: Texaco Chemical Company, White Plains, N.Y.

[21] Appl. No.: 324,118

[22] Filed: Mar. 17, 1989

[51] Int. Cl.$^4$ .............................................. C07C 45/53
[52] U.S. Cl. ..................................... 568/385; 568/798
[58] Field of Search .............................. 568/385, 798

[56] References Cited

U.S. PATENT DOCUMENTS 4,490,565 12/1984 Chang et al. ........................ 568/798
4,490,566 12/1984 Chang et al. ........................ 568/798

FOREIGN PATENT DOCUMENTS 992508 1/1983 U.S.S.R. .............................. 568/385

OTHER PUBLICATIONS

Augustin Pop et al, Chem. Abst., vol. 107, #236170j (1987).
Asen'eva et al, Chem. Abst., vol. 97, #72015t (1982).
Bruk et al, Chem. Abst., vol. 101, #93231t (1984).

Primary Examiner—James H. Reamer
Attorney, Agent, or Firm—Jack H. Park; Kenneth R. Priem; Cynthia L. Kendrick

[57] ABSTRACT

A method is disclosed for the synthesis of phenol and acetone by acid-catalyzed decomposition over a catalyst comprising an acidic montmorillonite silica alumina clay, modified with a compound from the group consisting of a heteropoly acid, or the inorganic salt of zirconium, titanium and aluminum. The method allows for a 6-fold improvement in rate using heteropoly acid modified montmorillonite clays and a six to 10-food improvement is observed using zirconium or titanium, respectively.

22 Claims, 6 Drawing Sheets

× FRESH CLAY-24
⊙ USED CLAY-24
△ REGENERATED CLAY-24

METHOD FOR PRODUCTION OF PHENOL/ACETONE FROM CUMENE HYDROPEROXIDE

CROSS-REFERENCE

This application is related to U.S. patent application Ser. Nos. 07/261,817, 07/261,818 and 07/261,819, filed Oct. 24, 1988.

This invention relates to improvements in methods for decomposition of organic hydroperoxides, and more particularly this invention relates to a method for producing phenol and acetone by decomposition of cumene hydroperoxide over a modified montmorillonite acidic clay catalyst. The montmorillonite acidic clay is modified with a heteropoly acid or titanium, zirconium or aluminum. The invention is particularly advantageous in that the decomposition takes place at mild temperatures and phenol is generated in at least as high as 99% mole yield. The catalyst is very attractive in that it is relatively inexpensive, by-products are produced in a much smaller percentage than with standard acid catalysis and the system solves many problems currently encountered in commercial systems regarding sulfur dioxide.

BACKGROUND OF THE INVENTION

It is known to those skilled in the art that cumene can be oxidized to cumene hydroperoxide and that cumene hydroperoxide can be decomposed by various means to provide phenol and acetone.

In the past certain acid catalysts have been used for producing phenol and acetone. In the cases where acidic substances are utilized as the catalysts the yields are satisfactory, however many of these acid catalysts require substantial expenditure for production of phenol and acetone, there are disposal problems with spent acids or their salts, and there are difficulties in achieving >99.9% purity phenol required by today's market place due to entrainment or breakthrough of said acids. In addition, by-products such as mesityl oxide, α-methylstyrene, acetophenone and 2-phenyl-2-propanol are produced along with the product and must somehow be removed and processed.

The use of clays in catalysis is also known.

In an article titled "Catalysis: Selective Developments", *Chem. Systems Report* 84-3, 239-249, at Section 3.4320, the unusual properties of smectite clays which make them of interest as catalysts are discussed. These compositions are layered and exhibit a 2:1 relationship between tetrahedral and octahedral sites. In addition, the combination of cation exchange, intercalation and the fact that the distance between layers can be adjusted provide interesting possibilities.

There is a discussion of clay mineral catalysts, including "acid" montmorillonite clay catalysts in "Progress in Inorganic Chemistry", Vol. 35, p. 41 (1987). The process of pillaring this type of catalyst is discussed. Pillaring can convert a clay lamellar solid into a more heat resistant two dimensional zeolite material.

U.K. patent application No. 2,179,563 (1987) discloses the use of modified, layered clay catalysts in reactions capable of catalysis by protons. The particular suitability of montmorillonite clays is discussed.

The use of stabilized pillared interlayered clays as catalysts in reactions capable of catalysis by protons is disclosed in European patent application 0,083,970.

In U.S. Pat. No. 4,665,044 to Pinnavaia, et al., modified clays containing 6.1 to 9.8 ferric ions per cell are prepared by contacting an aqueous slurry of layered lattice clay with a hydrolyzed solution of ferric ion.

In related U.S. Pat. No. 4,665,045 a catalyst is prepared which is similar to that of '044, but contains chromium ions.

In an article in *J. Mol. Catal.*, 27 (1984) 195, Pinnavaia, et al. discuss the pillaring and delamination of smectite clay catalysts by polyoxocations of aluminum. The results of the work demonstrate that pore openings of pillared montmorillonite and montronite clays are determined principally by the method used to dry the flocculated reaction products.

In an article titled "Synthesis of Interlamelar Montmorillonitediphenylphosphine Triosmium Cluster Complexes" in *Appl. Catal.*, 1987, 35, 177 Choudary et al. disclose that clays can be used as alternatives to polymers and inorganic oxides as supports for clusters.

In European patent application 0 250 168 a method is disclosed for production of glycol ethers by reacting an olefin oxide with an alkanol over a cation-exchangeable lamellar clay catalyst wherein the exchangeable cations of the catalyst are cations of one or more rare earth elements.

Gaaf, et al. discuss work showing that nickel substituted mica montmorillonite (Ni-SMM) clay can be intercalated successfully with aluminum and silica-alumina oligomers leading to pillared clays; transmission electron microscopy has revealed agglomeration of the particles which leads to suppression of hydroisomerization catalysis. See *J. Chem. Soc. Chem. Comm.*, 655, 1983.

In *J. Am. Chem. Soc.*, 1985 107, 4783, Pinnavaia et al. discuss properties of chromia pillared clay catalysts which exhibit gallery heights that are about 3.0 Å larger than those of zirconia and alumina pillared clay catalysts.

There is a good overview of the use of pillared cation-exchanged and acid-heated montmorillonite catalysts in *Applied Clay Science*, 2, (1987), p. 309.

A catalytic application of smectite clays is discussed in an article titled "Catalysis of Friedel-Craftrs, Alkylation by a Montomorillonite Doped with Transition-Metal Cations" in *Helvetica Chimica Acta*, 70 (1987), p. 577. Here a process is disclosed for obtaining catalysts by the exchange of interstitial cations in the K-10 montmorillonite for use in alkylations with halides, alcohols and olefins. It was found that the efficiency of the catalyst bears no apparent relation to the corresponding Lewis acids under homogeneous conditions. Zirconium and titanium gave the best results in this study.

It would be a substantial advance in the art if phenol and acetone could be produced in yields approaching 100% by decomposition over an inexpensive catalyst using mild conditions. A catalyst which worked at very high space velocities using mild conditions and yet afforded high selectivities and yields with a smaller percentage of by-products would be particularly advantageous. Furthermore a very active, long life catalyst would also solve the catalyst disposal and acid entrainment problems referred to above.

SUMMARY OF THE INVENTION

In accordance with the foregoing, the novel method of this invention for continuous cogeneration of phenol and acetone comprises reacting cumene hydroperoxide in the presence of a catalyst comprising a modified montmorillonite acidic clay which has been modified with materials selected from the group consisting of heteropoly acids, titanium, zirconium or aluminum, at mild temperature and pressure. Examples demonstrate the effectiveness of, for example, tungstophosphoric acid on montmorillonite acidic clays and zirconium and titanium modified montmorillonite silica-alumina clays.

A particular advantage of the instant invention over previous methods is that in the instant invention many problems previously encountered involving $SO_2$ are solved. There are no $SO_2$ disposal problems; $SO_2$ breakthroughs and $SO_2$ corrosion are not problems and a greatly improved yield is observed. Every 1% yield improvement interprets into substantial cost savings in a typical plant operation. A 6-fold improvement in reaction rate is observed with heteropoly acid modified montmorillonite acidic clays and as much as a 10-fold improvement is observed using titanium modified clay. The method of the instant invention allows for quantitative conversions with yields of up to 99 mole % or better. In addition, LHSVs of 10 or greater have also been demonstrated.

DESCRIPTION OF THE INVENTION

Preparation of the product of this invention may be carried out typically by reacting cumene hydroperoxide continuously in the presence of a decomposition catalyst comprising modified acidic montmorillonite clay. In the first embodiment, the catalyst preferably comprises a montmorillonite silica-alumina clay modified by use of a heteropoly acid and in the second embodiment the clay is modified with titanium, zirconium or aluminum. Either catalyst may be in powdered, granular or extruded form.

The reaction can be represented by the following:

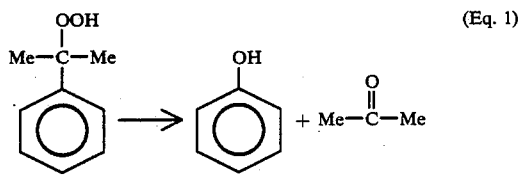
(Eq. 1)

The same method may also be applied to the reaction of other hydroperoxides. For example, the process may be applied to the decomposition of aromatic hydroperoxides such as sec-butylbenzene hydroperoxide, ethylbenzene hydroperoxide and cyclohexylbenzene hydroperoxide.

The clays used as the base of the catalysts to effect this reaction are montmorillonite silica-alumina clays. A variety of clay catalysts containing aluminum and silica are effective in the subject reaction (Eq. 1), however it is necessary that the alumina or silica be acidic under normal operating conditions. As discussed, a group of catalysts which works well in this synthesis are acidic clay mineral catalysts. Chemically clays are composed primarily of silicon, aluminum and oxygen, with minor amounts of magnesium and iron in some cases. Variations in the ratios of these constituents, and their crystal lattice configurations, result in some fifty separate clays, each with its own characteristic properties.

Particularly effective in the reaction of Equation 1 are smectite clays. Smectite clays are discussed in the article cited in Chem. Systems Report, 84-3. These clays have small particle size and unusual intercalation properties which afford them high surface area. They are alumino silicates having a unique structure that permits modifications which provide useful catalysts. They comprise layered sheets of octahedral sites between sheets of tetrahedral sites, and the distance between the layers can be adjusted by swelling, through treatment with the appropriate solvent, or treatment with a pillaring or Lewis acid reagent etc. What renders the smectites of particular interest among the clay minerals is their combination of cation exchange, intercalation and swelling properties.

The three-layer sheet types of smectite clays include montmorillonite, vermiculite and certain micas, all of which may be expanded between their layers by the appropriate treatment. The idealized basic structure of clays of this type is that of a pyrophyllite which has the basic formula $Si_8Al_4O_{20}(OH)_4$.

A general representation of the montmorillonite structure which is particularly useful is:

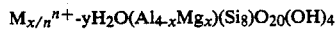

where M represents the interlamellar (balancing cation, normally sodium or lithium) and x, y and n are integers.

These montmorillonite clays are best used in the present application in an acidic form. Acids activate montmorillonites by attacking and solubilizing structural cations in the octahedral layers. This opens up the clay structure and increases surface area. In the first embodiment heteropoly acids are used to modify the clay. These acid treated clays act as strong Bronsted acids. In the second embodiment titanium, zirconium and aluminum derivatives which act as Lewis acids are used to modify the clay.

Acidic montmorillonite clays are the preferred form of smectite clay in the present invention. Preferably these acid clays should have acidities in the range of 3 to 15, or greater, mg KOH/gm, titrated to a phenolphthalein end point. Their surface area should be $>30$ m$^2$/g, and preferably 200 to 1000 m$^2$/g. Their moisture content should be limited also, thereby upon heating to 220° F., the weight loss is generally less than 20 wt. %.

Illustrative examples of suitable montmorillonite clays include powdered clays such as Filtrol Grade 13, 113 and 160, sold by Engelhard, clays in granular form, such as Filtrol Grade 24, having a 20–60 mesh size, and grade 25 (10/20 mesh) sold by Engelhard, as well as extruded clays such as the Filtrol Clay-62, sold in 1/16" and 3/16" diameter extrudates.

In the first embodiment where heteropoly acids are used to modify the clays, the heteropoly acids comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 2:

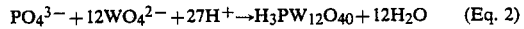

A wide variety of elements ranging from Group I to Group VIII can become the central atom of the HPA anion, or the heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Equation 2) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature [see for example U.S. Pat. No. 3,947,323 (1976)].

TABLE 1

| Typical heteropolymolybdate anions | | |
|---|---|---|
| CONDENSATION RATIOS | HETERO ATOMS (X) | CHEMICAL FORMULAS |
| 1:12 Keggin structure | $P^{5+}$, $As^{5+}$, $Si^{4+}$, $Ge^{4+}$ | $[X^{n+}Mo_{12}O_{40}]^{-(8-n)}$ |
| Silverton structure | $Ce^{4+}$, $Th^{4+}$ | $[X^{4+}Mo_{12}O_{42}]^{8-}$ |
| 1:11 Keggin structure (decomposition) | $P^{5+}$, $As^{5+}$, $Ge^{4+}$, $Si^{4+}$ | $[X^{n+}Mo_{11}O_{39}]^{-(12-n)}$ |
| 2:18 Dawson structure | $P^{5+}$, $As^{5+}$ | $[X_2^{5+}Mo_{18}O_{62}]^{6-}$ |
| 1:9 Waugh structure | $Mn^{4+}$, $Ni^{4+}$ | $[X^{4+}Mo_9O_{32}]^{6-}$ |
| 1:6 Anderson structure (A type) | $Te^{6+}$, $I^{7+}$ | $[X^{n+}Mo_6O_{24}]^{-(12-n)}$ |
| (B type) | $Co^{3+}$, $Al^{3+}$, $Cr^{3+}$ | $[X^{n+}Mo_6O_{24}H_6]^{-(6-n)}$ |
| 4:12 | $As^{5+}$ | $[H_4As_4Mo_{12}O_{52}]^{4-}$ |
| 2:5 | $P^{5+}$ | $[P_2Mo_5O_{23}]^{6-}$ |

In the case of conversion of cumene hydroperoxide to phenol/acetone, suitable heterpoly acid catalysts may contain polyatoms selected from the group molybdenum, tungsten, niobium and vanadium, while the heteroatoms may be phosphorus, silicon, germanium, and arsenic. Preferably the heteroatoms are phosphorous or silicon. These heteropoly acids would likely have the Keggin structure, $H_{8-n}[XM_{12}O_{40}]$, where X=P or Si, M=Mo or W and n is an integer which is 4 or 5.

The preferred heteropoly acids for the practice of this invention include 12-molybdophosphoric acid, $H_3PMo_{12}O_{40}$, 12-tungstophosphoric acid, molybdosilicic acid, $H_4SiMo_{12}O_{40}$ and 12-tungstosilicic acid. Said acids are generally used as their hydrates and the clay is added to the aqueous solution in granular form. Stirring is maintained for 1-2 days at room temperature. The mixture is then filtered, the solids washed with distilled water until the washings contain no detectable levels of heteropoly acid and the final product is dried in vacuo at 40° C.

In the second embodiment of this invention it has been surprisingly discovered that the generation of phenol/acetone by commercially available acidic montmorillonite clays such as those outlined above is improved significantly by modification of the clays with a Group III or IV compound preferably from the group consisting of zirconium, titanium or aluminum. The rate of reaction exhibits between a 6-fold and 10-fold improvement.

The preparation of the zirconium, titanium or aluminum-modified clay catalyst is accomplished by treating an acidic montmorillonite clay, such as, for example Engelhard Clay-24 with an aqueous or alcoholic solution of the Group III or IV metal as a salt of an inorganic acid. For example granular montmorillonite clay can be added to an aqueous or alcoholic solution or suspension of zirconium(IV) chloride, titanium(IV) chloride or aluminum nitrate. Said salts may be partially hydrolyzed during this addition. Stirring is typically maintained for 1-2 days at about room temperature, but this time period can be shorter. The mixture is then filtered, the solids washed until the washings no longer show detectable levels of metal ions and the final product dried in vacuo at 40° C.

The cumene hydroperoxide decomposition may be conducted batchwise, in a continuous slurry bed reactor, or in a fixed-bed, continuous flow, reactor. For practical reasons a fixed bed process is preferred. In all cases the catalyst concentration should be sufficient to provide the desired catalytic effect.

Cogeneration of phenol and acetone can generally be conducted at temperatures from 20° to 150° C.; the preferred range is 40° to 120° C. The operating pressure may be from zero to 1000 psig, or higher. The preferred pressure range is 100 to 400 psig. Because of the highly exothermic nature (52 Kcal/mole) of the cumene hydroperoxide decomposition (Eq. 1), temperature control is particularly important, especially in a fixed catalyst bed process.

Typically, phenol is generated continuously in up to ca. 50 wt. % concentration in the crude product liquid effluent, and likewise, acetone may be generated in up to 40 wt. % concentrations. The cumene hydroperoxide should preferably be as pure as possible, but an 80% purity is certainly acceptable. Typical impurities in such an "80%" cumene hydroperoxide feed are cumene, 2-phenyl-2-propanol and acetophenone. Said cumene hydroperoxide is generally diluted with inert solvent, or product, prior to being fed to the decomposer. Typical diluents include acetone, or a mix of acetone, cumene and phenol.

Generally cumene hydroperoxide conversions are quantitative in continuous unit operations. Phenol yields, based on hydroperoxide charged, are many times 99 mole % or better. Likewise, acetone yields are also 99 mole % or better.

These yields are achieved at total liquid hourly space velocities (LHSV) of one to 10 under mild conditions. LHSVs of 60, or greater, have also been demonstrated to be useful in achieving quantitative cumene hydroperoxide conversion.

Here LHSV is defined as follows:

$$LHSV = \frac{\text{Weight Of Total Liquid Feed Run Through The Reactor Per Hour}}{\text{Volume of Catalyst In Reactor}}$$

The examples which follow illustrate the cogeneration of phenol and acetone from cumene hydroperoxide using montmorillonite clay catalysts which have been modified with heteropoly acids or zirconium, titanium or aluminum.

Conversion of cumene hydroperoxide (wt. %) is estimated in the following examples using the equation:

$$\frac{[\text{Wt \% Conc. of } (C_6H_5C(CH_3)_2OOH \text{ in Feed} - \text{Wt \% Conc. of Cumene Hydroperoxide in product}]}{\text{Wt \% Conc. of Cumene Hydroperoxide in Feed}} \times 100$$

Yields of phenol/acetone ($C_6H_5OH/CH_3COCH_3$, mole %) are estimated from:

$$\frac{\text{Moles of Phenol or Acetone in Product Liquid}}{\text{Moles of Cumene Hydroperoxide in feed}} \times 100$$

A third aspect of this invention involves a novel method for the regeneration of spent montmorillonite clay catalysts. It has been discovered that said catalysts can be regenerated by:

(1) Treatment with concentrated nitric acid, or by treatment with methanol.

(2) Treatment in this manner is surprisingly effective in that after treatment with nitric acid, in particular, the catalyst demonstrates:
   (a) Improved phenol productivity;
   (b) Improved levels of cumene hydroperoxide conversions;
   (c) The catalyst exhibits higher ash content and therefore lower levels of organic contaminants;
   (d) The catalyst exhibits an improved color which indicates lower levels of organic polymers;
   (e) In some cases the regenerated clay catalyst has a higher activity than the control samples of fresh catalyst.

Examples 17 through 20 illustrate the regeneration of a clay catalyst such as Engelhard Clay, Grade 24 by Soxlet extraction with concentrated nitric acid, and by treatment with methanol.

The data in Examples 1 through 7 illustrate:

a. The preparation of 12-tungstophosphoric acid-modified clay (Example 1).

b. Phenol/acetone generation using an unmodified montmorillonite clay catalyst in a typical batch synthesis with a small (standard) quantity of catalyst charged (see Comparative Example A).

c. A second Comparative Example, demonstrates a lack of reaction in the absence of any clay catalyst (Comparative Example B).

d. Phenol/acetone generation using the 12-tungstophosphoric acid-modified Clay-24 catalyst of Example 1. This gives at least a 6-fold improvement in rate of comparison with the unmodified clay (compare Examples 2 and A).

e. Phenol/acetone generation using a series of three other heteropoly acid modified Clay-24 catalysts, prepared by the procedure of Example 1 and tested by the procedure of Example 2. These catalysts, including 12-molybdophosphoric acid, 12-molybdosilicic acid and 12-tungstosilicic acid on Clay-24, typically give a 6-fold improvement in rate of comparison with the unmodified clay (compare Examples 3-5 versus A).

f. Preparation of a 12-tungstophosphoric acid modified Clay-62, in extruded form (Example 6).

g. The use of the 12-tungstophosphoric acid clay extrudates in the continuous generation of phenol/acetone at high space velocities and low operating temperatures (see Example 7). Here phenol and acetone yields are $\geq 99$ mole %.

It is understood that the examples given are only for illustration and that the instant invention is not intended to be limited thereby.

EXAMPLE 1

Preparation of 12-Tungstophosphoric Acid Modified Clay

To a 100 cc aqueous solution of 12-tungstophosphoric acid (0.1N, containing 28.8 g of $H_3PO_4 \cdot 12WO_3 \cdot xH_2O$) is added with stirring 10 g of granular montmorillonite clay (Grade 24, from Engelhard Corporation). Stirring is maintained for 1–2 days at room temperature (20° C.). The mixture is then filtered and the solids washed with distilled water until the washings no longer show detectable levels of tungsten, and the final product dried in vacuo at 40° C. About 8.7 g of tungstophosphoric acid-modified clay is recovered. Tungsten content is analyzed to be 1.0 wt. %.

COMPARATIVE EXAMPLE A

Phenol/Acetone Generation using Unmodified Clay Catalyst

To a 250-ml round bottom flask fitted with a condenser, heater, stirrer and feed control, is charged a mixture of 60.0 g of acetone and 0.1 g of Engelhard Clay-24. The mixture is heated to reflux (57° C.) with stirring, and 40.0 g of "80%" cumene hydroperoxide solution added dropwise such that the pot temperature does not exceed 66° C.

Small samples ($\approx 2$ ml) of the reactant solution are withdrawn at regular periods and analyzed by glc.

The composition of the "80%" cumene hydroperoxide feed is:

| | |
|---|---|
| Cumene hydroperoxide | 78.5% |
| Cumene | 16.5% |
| 2-phenyl-2-propanol | 4.7% |
| Acetophenone | 0.4% |

The phenol content of the reactant solution is illustrated in FIG. 1. After 1 hour reaction time:

Estimated cumene hydroperoxide conversion is $\approx 24\%$.

Estimated phenol yield is $\approx 23$ mole %.

Composition of the product solution after 1 hour is:

| | |
|---|---|
| Acetone | 64.4 wt % |
| Cumene | 5.1 wt % |
| Methyl styrene | 0.1 wt % |
| Phenol | 4.5 wt % |
| 2-phenyl-2-propanol | 1.8 wt % |
| Acetophenone | 0.2 wt % |
| Cumene hydroperoxide | 23.8 wt % |

COMPARATIVE EXAMPLE B

Phenol/Acetone Generation Without Catalyst

Following the procedures of Comparative Example A, 40.0 g of "80%" cumene hydroperoxide is diluted with acetone (60.0 g) and heated to reflux (66° C.) in the absence of any added clay catalyst.

Samples taken after 1 hour show:

| | |
|---|---|
| Cumene hydroperoxide conversion | = <1% |
| Phenol content | = <0.1 wt % |

-continued

| Estimated phenol yield | = <0.1% |

EXAMPLE 2

Phenol/Acetone Generation using 12-Tungstophosphoric Acid Modified Clay

To a 250-ml round-bottom flask fitted with a condenser, heater, stirrer and feed control, is charged a mixture of 60.0 g of acetone and 0.1 g of the 12-tungstophosphoric acid modified clay of Example 1. The mixture is heated to reflux (57° C.) with stirring and 40.0 g of the 80% cumene hydroperoxide solution of comparative Example A added dropwise such that the pot temperature does not exceed 66° C.

Small samples ($\approx$2 ml) of the reactant solution are withdrawn at regular periods and analyzed by glc.

Figure 2:
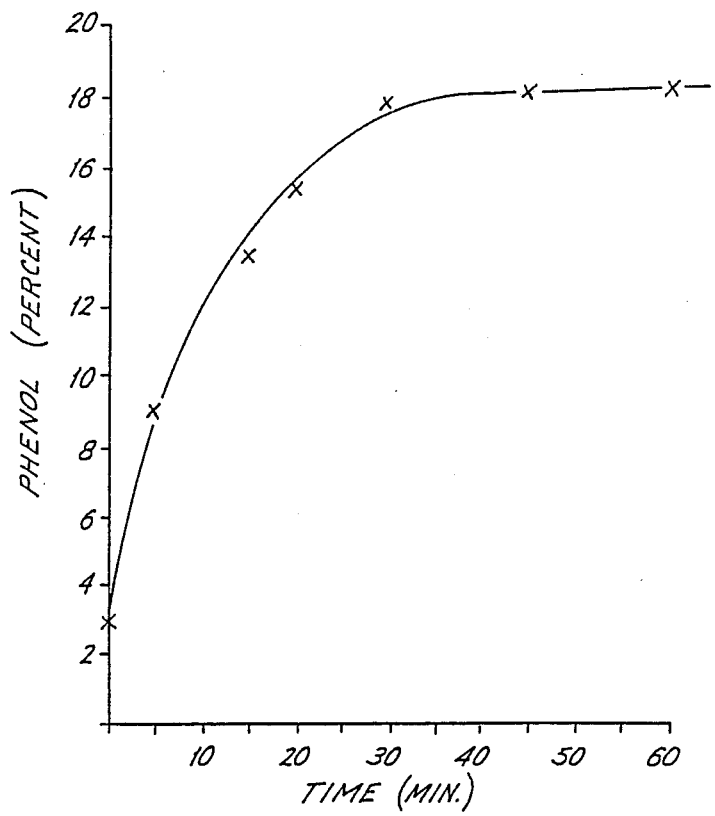

The phenol content of the reactant solution is illustrated in FIG. 2. After 30 minutes reaction time:

| Estimated cumene hydroperoxide conversion | = 96% |
| Estimated phenol yield | = 95 mole % |

Composition of the product solution after 30 minutes is:

| Acetone | 72.8 wt % |
| Cumene | 5.4 wt % |
| α-Methyl styrene | 0.1 wt % |
| Phenol | 18.5 wt % |
| 2-phenyl-2-propanol | 1.4 wt % |
| Acetophenone | 0.2 wt % |
| Cumene hydroperoxide | 1.3 wt % |

The estimated rate of phenol formation with the tungstophosphoric acid modified clay in this example is at least 6 times faster than with the unmodified clay of comparative Example A.

EXAMPLES 3-5

Phenol/Acetone Generation using other Heteropoly Acid Modified Clay Catalysts Following the procedures of Example 2, to a 250-ml round-bottom flask fitted with condenser, heater, stirrer and feed control, is charged a mixture of 60.0 g of acetone and 0.1 g of heteropoly acid (12-molybdophosphoric acid, 12-tungstosilicic acid and 12-molybdosilicic acid) modified Clay-24 prepared by the method of Example 1. The mixture is heated to reflux (57° C.) with stirring and 40.0 g of the 80% cumene hydroperoxide solution of Comparative Example A added dropwise such that the pot temperature does not exceed 68° C.

Small samples ($\approx$2 ml) of the reactant solution are withdrawn at regular periods and analyzed by glc.

Figure 3:
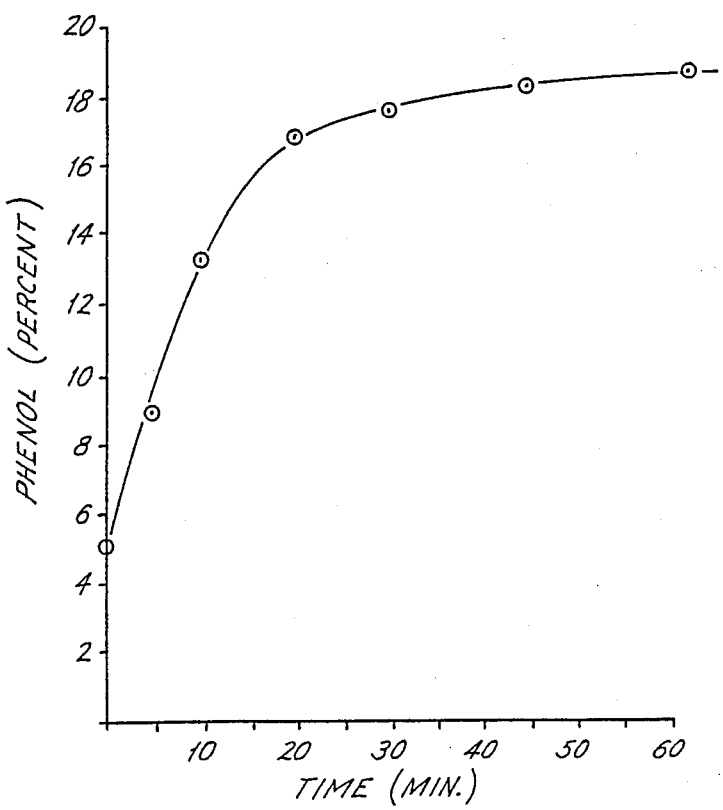
Figure 4:
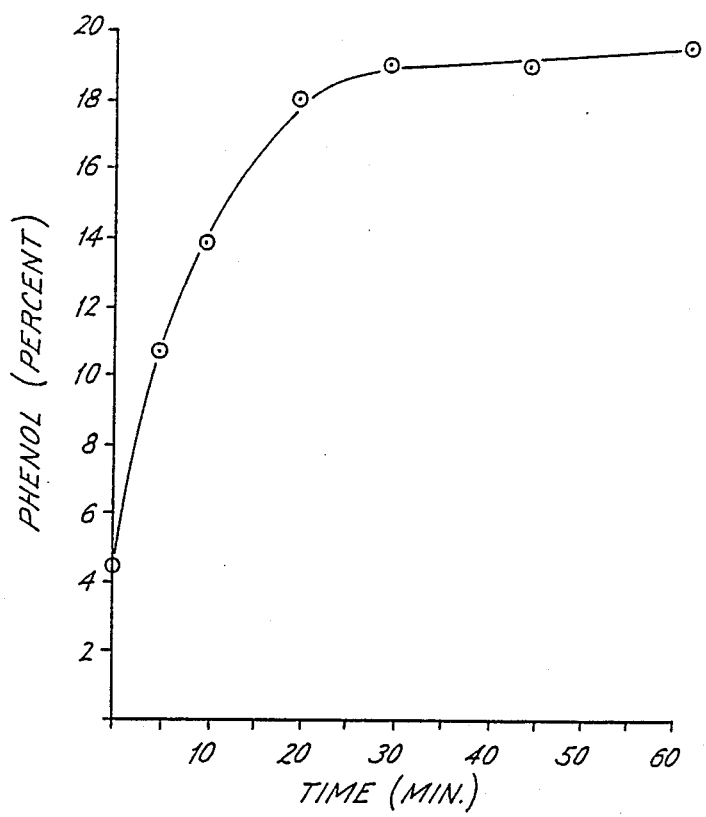
Figure 5:
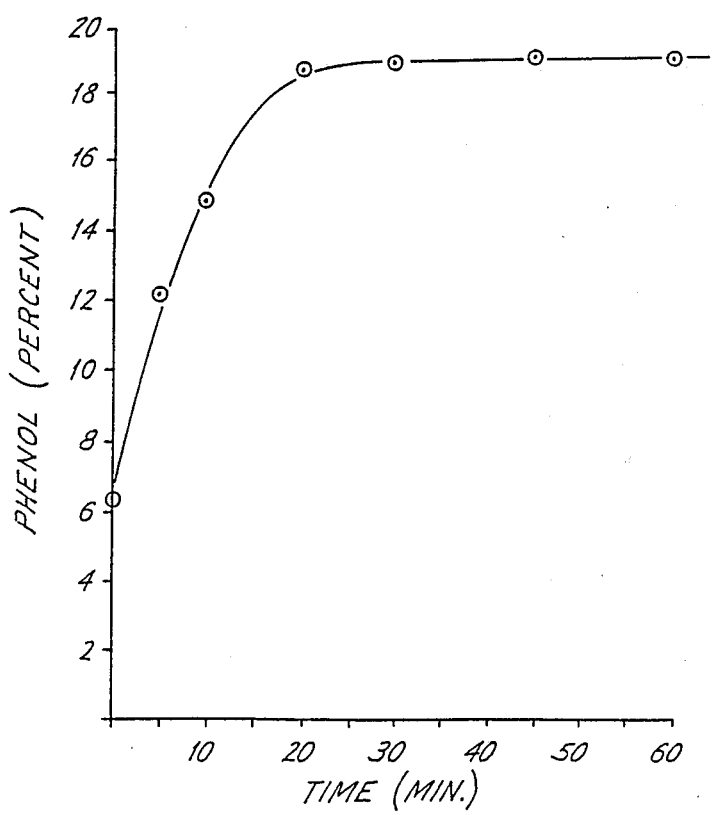

The phenol content of the reactant solutions is illustrated in the accompanying FIGS. 3-5, and the compositions of the product solutions after 1 hour are summarized in Table II.

Again, it may be noted that the rate of phenol formation with each of these three heteropoly acid-modified Clay-24 catalysts is at least six times faster than with the unmodified Clay-24 of Comparative Example A.

EXAMPLE 6

Preparation Of Tungstophosphoric Acid Modified Clay

To a 2-liter aqueous solution of 12-tungstophosphoric acid (0.0N, containing 57.6 g of $H_3PO_4$ $WO_3$ $xH_2O$) is added with stirring 200 g of extruded montmorillonite clay (Grade 62, from Engelhard, 1/16" extrudates). Stirring is maintained for 2 days at room temperature. The extrudates are then recovered by filtration, washed with distilled water until tungsten is no longer detected in the washings, dried in vacuo at 40° C., and sieved through #10 and 20 mesh screens.

Tungsten content of the finished extrudates is 0.3 wt. %.

EXAMPLE 7

Phenol/Acetone Generation Using 12 Tungstophosphoric Acid Modified Clay Catalyst To a continuous, plug flow reactor equipped with heating/cooling capabilities is charged 150 cc of the 12-tungstophosphoric acid-modified Clay-62 catalyst of Example 6. The catalyst is pretreated with a stream of acetone at 60° C., and then 80% cumene hydroperoxide of Example A, diluted with an acetone/cumene/phenol mix is passed through the catalyst bed in the upflow mode at a reactor temperature of 60° C. and a series of three feed flow rates.

Composition of the feed and product solutions are summarized in Table III.

In the case Sample #7, run at a feed LHSV of 10:

| Estimated phenol yield | = 99 mole % |
| Estimated acetone yield | = >99 mole % |

TABLE II

| EXAMPLE | CATALYST | PRODUCT LIQUID COMPOSITION (WT %)[b] | | | | | | | YIELD (MOLE %) |
| | | ACETONE | CUMENE | α-METHYL STYRENE | PHENOL | 2-PHENYL 2-PROPANOL | ACETOPHENONE | CUMENE HYDROPEROXIDE | |
| --- | --- | --- | --- | --- | --- | --- | --- | --- | --- |
| 3 | $H_3PO_4.12MoO_3$/Clay-24 | 74.0 | 5.2 | 0.3 | 18.7 | 1.0 | 0.2 | 0.1 | 96 |
| 4 | $H_4SiO_4.12MoO_3$/Clay-24 | 73.7 | 4.8 | 0.3 | 19.6 | 1.1 | 0.2 | — | >99 |
| 5 | $H_4SiO_4.12WO_3$/Clay-24 | 74.0 | 4.8 | 0.3 | 19.2 | 1.1 | 0.2 | 0.1 | 99 |

[a]Heteropoly acid on Clay-24 catalyst prepared according to the procedure of Example 1.
[b]After 1 hour reaction time.

TABLE III

| CATALYST | PRESSURE (PSIG) | TEMP<sup>a</sup> DOW THERM BED | FEED RATE LB/HR | SAMPLE | ACETONE | MESITYL OXIDE | CUMENE | PHENOL | ALPHA-METHYL STYRENE | ACETO-PHENONE | 2-PHENYL 2-PROPANOL | CUMENE HYDRO-PER-OXIDE | 4-CUMYL PHENOL |
|---|---|---|---|---|---|---|---|---|---|---|---|---|---|
| Example 6<sup>a</sup> | 300 | 60 | 0.99 | 1 | 34.8 | — | 13.0 | 50.4 | 0.7 | 0.2 | 0.1 | — | 0.4 |
| | | | | 2 | 34.8 | — | 13.0 | 50.5 | 0.7 | 0.2 | 0.1 | — | 0.3 |
| | | | | 3 | 29.7 | — | 13.6 | 54.9 | 0.8 | 0.2 | 0.1 | — | 0.4 |
| | | | 1.65 | 4 | 34.8 | — | 13.0 | 50.4 | 0.7 | 0.2 | 0.1 | — | 0.3 |
| | | | | 5 | 35.0 | — | 13.0 | 50.3 | 0.7 | 0.2 | 0.1 | — | 0.4 |
| | | | | 6 | 34.0 | — | 13.1 | 51.2 | 0.7 | 0.2 | 0.1 | — | 0.3 |
| | | | 3.3 | 7 | 34.7 | — | 13.0 | 50.3 | 0.8 | 0.2 | 0.1 | 0.1 | 0.4 |
| | | | | 8 | 34.8 | — | 13.0 | 50.2 | 0.8 | 0.2 | 0.1 | 0.2 | 0.4 |
| | | | | 9<sup>b</sup> | 35.0 | — | 13.1 | 50.1 | 0.7 | 0.2 | 0.1 | 0.3 | 0.3 |
| Feed | | | | 1 | 25.8 | — | 13.2 | 37.0 | — | 0.1 | 1.7 | 22.2 | — |
| | | | | 2 | 26.0 | — | 13.2 | 36.6 | — | 0.1 | 1.7 | 22.3 | — |
| | | | | 3 | 26.0 | — | 13.2 | 36.7 | — | 0.1 | 1.7 | 22.2 | — |

<sup>a</sup>Tungstophosphoric acid treated Clay-62
<sup>b</sup>Recovered catalyst extremely clean, % ash - 87.0

The data in Examples 8 through 16 illustrate:
a. The preparation of zirconium(IV) chloride- and titanium(IV) chloride-modified clays (see Examples 8 and 9).
b. Phenol/acetone generation using the zirconium-modified clay catalyst of Example 8 —this gives at least a 6-fold improvement in rate in comparison with the unmodified clay (cf. Examples 10 and A).
c. Phenol/acetone generation using the titanium-modified clay catalyst of Example 9 which this gives at least a 10-fold improvement in rate in comparison with the unmodified clay (cf. Examples 11 and A).
d. Phenol/acetone generation using the aluminum-modified clay catalyst where the aluminum source is $Al(NO_3)_3$—this catalyst also improves the rate in comparison with the unmodified clay (cf. Examples 12 and A).
e. Phenol/acetone generation using an aluminum(III) chloride-modified clay catalyst—again there is an improvement in rate (Example 13).
f. Phenol/acetone generation using a clay catalyst modified with an ethanolic solution of zirconium-(IV) chloride (Example 14).
g. Preparation of a titanium(IV) chloride modified clay in extrudate form (Example 15).
h. The use of the titanium-modified clay extrudates in the continuous generation of phenol/acetone at high space velocities and low operating temperatures (see Example 16).

EXAMPLE 8

Preparation Of Zirconium(IV) Chloride Modified Clay

To a 1-liter aqueous solution of zirconium (IV) chloride (0.5N, containing 116 g of $ZrCl_4$) is added with stirring 100 cc of granular montmorillonite clay (Grade 24, from Engelhard Corporation). Stirring is maintained for 1–2 days at room temperature (20° C.).

The mixture is then filtered, the solids washed with distilled water until the washings no longer show detectable levels of zirconium ions, and the final product dried in vacuo at 40° C. About 90 g of zirconium-modified clay is recovered. Zirconium content is analyzed to be 6.9 wt. %.

EXAMPLE 9

Preparation Of Titanium(IV) Chloride Modified Clay

To a 100 cc aqueous solution of titanium(IV) chloride (0.5N, containing 9.5 g of $TiCl_4$) is added with stirring 10 g of granular montmorillonite clay (Grade 24, from Engelhard Corporation). Stirring is maintained for 2–3 days at room temperature.

The mixture is then filtered, the solids washed with distilled water until the washings no longer show detectable levels of titanium ions, and the final product dried in vacuo at 40° C. About 10.1 g of titanium-modified clay is recovered. Titanium content is analyzed to be 5.1 wt. %.

EXAMPLE 10

Phenol/Acetone Generation Using Zirconium-Modified Clay Catalyst

To a 250 ml round bottom flask fitted with a condenser, heater, stirrer and feed control, is charged a mixture of 60.0 g of acetone and 0.1 g of the zirconium-modified clay of Example 8. The mixture is heated to reflux (57° C.) with stirring and 40.0 g of the 80% cumene hydroperoxide solution of Comparative Example "A" added dropwise such that the pot temperature does not exceed 66° C.

Small samples ($\approx 2$ ml) of the reactant solution are withdrawn at regular periods and analyzed by glc.

Figure 6:
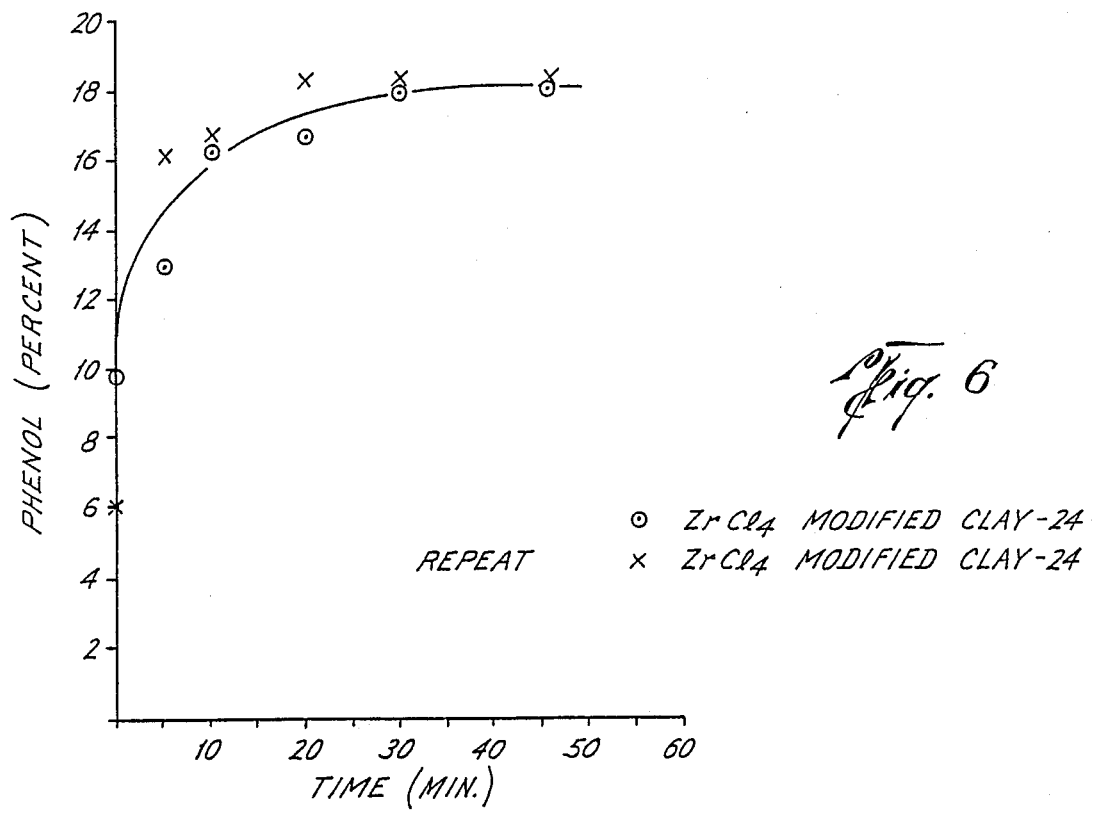

The phenol content of the reactant solution is illustrated in FIG. 6, @ data points. After 30 minutes reaction time:
Estimated cumene hydroperoxide conversion is=98%
Estimated phenol yield is=93 mole %
Composition of the product solution after 30 minutes is:

| Acetone | 73.3 wt % |
|---|---|
| Cumene | 5.9 wt % |
| Methyl styrene | 0.3 wt % |
| Phenol | 18.0 wt % |
| 2-phenyl-2-propanol | 1.3 wt % |
| Acetophenone | 0.2 wt % |
| Cumene hydroperoxide | 0.7 wt % |

A repeat run using a second sample of zirconium-modified clay catalyst is illustrated by the x data points in FIG. 6.

Again essentially all the cumene hydroperoxide has reacted in less than 30 minutes reaction time.

The estimated rate of phenol formation with the zirconium-modified clays in this example is at least 6 times faster than with the unmodified clay of Comparative Example "A".

EXAMPLE 11

Phenol/Acetone Generation Using Titanium-Modified Clay Catalyst

To a 250 ml round bottom flask fitted with a condenser, heater, stirrer and feed control, is charged a mixture of 60.0 g of acetone and 0.1 g of the titanium-modified clay of Example 9. The mixture is heated to reflux (57° C.) with stirring and 40.0 g of the 80% cumene hydroperoxide solution of Comparative Example "A" added dropwise such that the pot temperature does not exceed 68° C.

Small samples ($\approx 2$ ml) of the reactant solution are withdrawn at regular periods and analyzed by glc.

Figure 7:
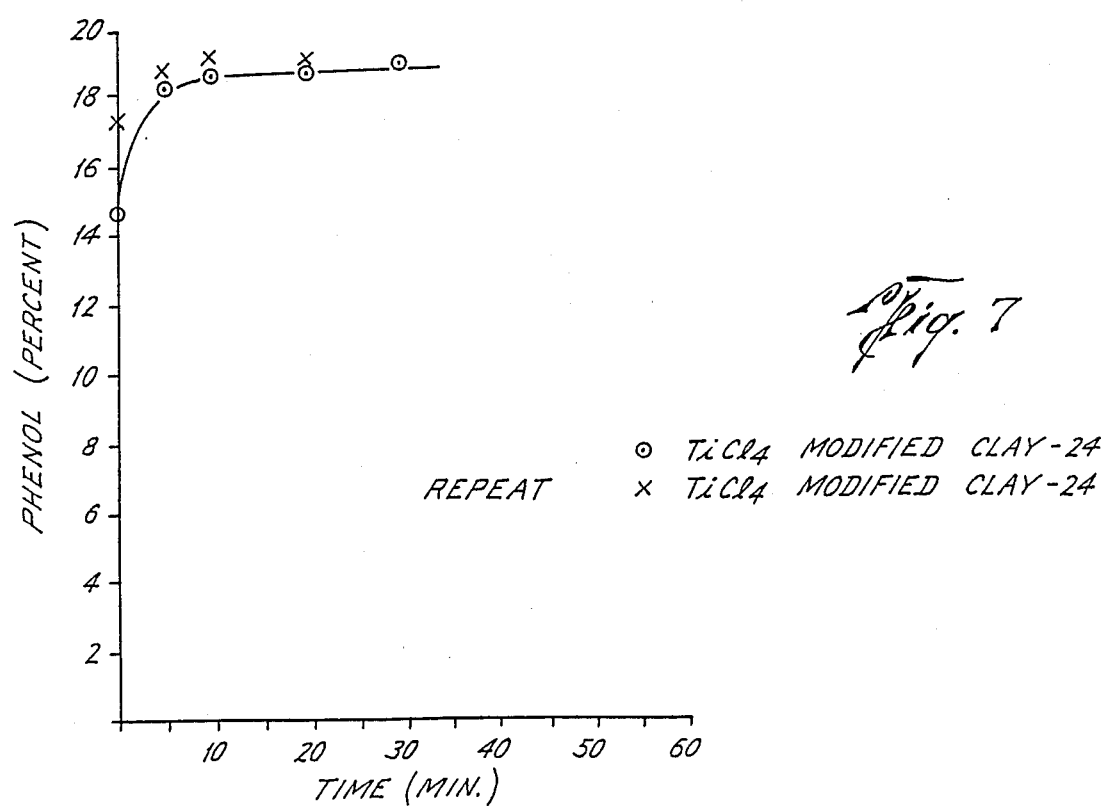

The phenol content of the reactant solution is illustrated in FIG. 7, @ data points. After 20 minutes reaction time:
Estimated cumene hydroperoxide conversion is=>99%
Estimated phenol yield is=96 mole %
Composition of the product solution after 20 minutes is:

| Acetone | 74.3 wt % |
|---|---|
| Cumene | 5.2 wt % |
| Methyl styrene | 0.6 wt % |
| Phenol | 18.6 wt % |
| 2-phenyl-2-propanol | 0.7 wt % |
| Acetophenone | 0.2 wt % |
| Cumene hydroperoxide | <0.1 wt % |

A repeat run using a second sample of titanium-modified clay catalyst is illustrated by the x data points in FIG. 7.

Again essentially all the cumene hydroperoxide has reacted in less than 20 minutes reaction time.

The estimated rate of phenol formation with the titanium-modified clays is at least 10 times faster in this example than with the unmodified clay of Comparative Example "A".

EXAMPLE 12

Phenol/Acetone Generation Using Aluminum-Modified Clay Catalyst

An aluminum-modified montmorillonite clay catalyst is prepared by treatment of Engelhard Clay-24 with an aqueous (0.5N) solution of aluminum(III) nitrate following the procedures of Example 8.

A 0.1 g sample of this aluminum-modified clay is then utilized as catalyst for the conversion of cumene hydroperoxide (40 g) to phenol/acetone following the procedures of Example 10.

After 1 hour reaction time:
Estimated cumene hydroperoxide conversion is = 98%
Estimated phenol yield is = >95 mole %
Composition of the present solution after 1 hours is:

| | |
|---|---|
| Acetone | 70.0 wt % |
| Cumene | 5.9 wt % |
| Methyl styrene | 0.3 wt % |
| Phenol | 22.3 wt % |
| 2-phenyl-2-propanol | 1.4 wt % |
| Acetophenone | 0.2 wt % |
| Cumene hydroperoxide | 0.7 wt % |

The estimated rate of phenol formation with the aluminum-modified clay of this example is about 5 times faster than with the unmodified clay of Comparative Example "A".

EXAMPLE 13

Phenol/Acetone Generation Using Aluminum-Modified Clay Catalyst

An aluminum-modified montmorillonite clay catalyst is prepared by treatment of Engelhard Clay-24 with an aqueous (0.5N) solution of aluminum(III) chloride following the procedures of Example 8.

A 0.1 g of this aluminum-modified clay is then utilized as catalyst for the conversion of cumene hydroperoxide (40 g) to phenol/acetone following the procedures of Example 10.

Figure 8:
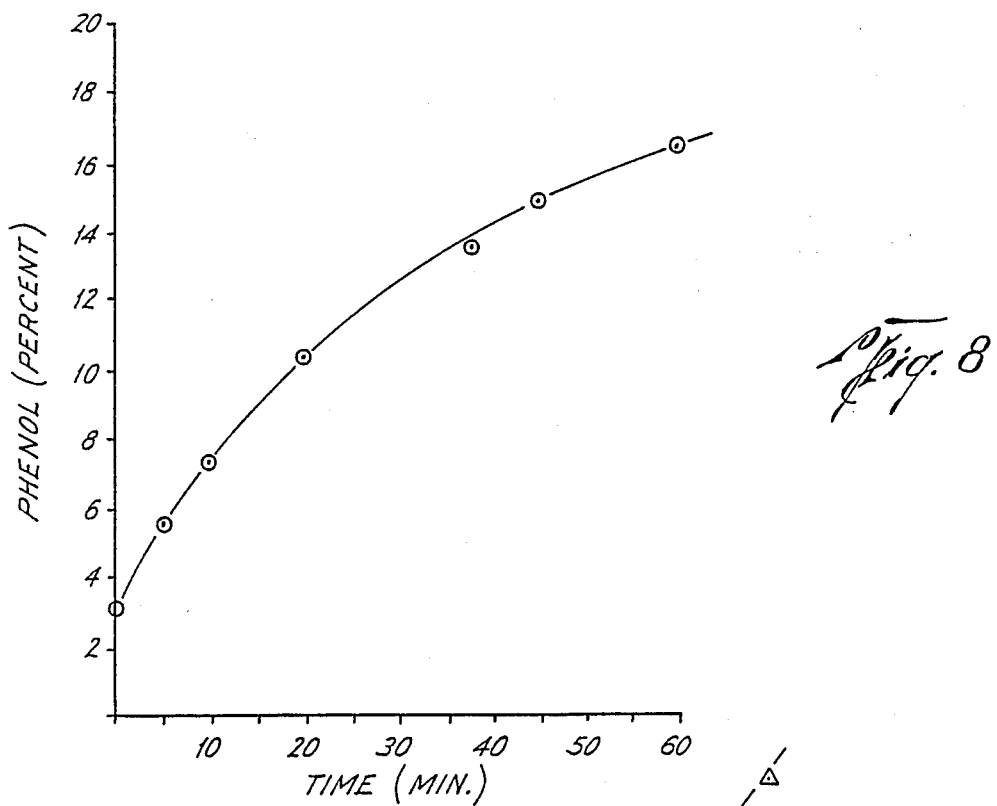

The phenol content of the reactant solution is illustrated in FIG. 8. After 1 hour reaction time:
Estimated cumene hydroperoxide conversion is = 92%
Estimated phenol yield is = 85 mole %
Composition of the product solution after 1 hour is:

| | |
|---|---|
| Acetone | 73 wt % |
| Cumene | 6.0 wt % |
| Methyl styrene | 0.1 wt % |
| Phenol | 16.5 wt % |
| 2-phenyl-2-propanol | 1.6 wt % |
| Acetophenone | 0.2 wt % |
| Cumene hydroperoxide | 2.4 wt % |

EXAMPLE 14

Phenol/Acetone Generation Using Zirconium-Modified Clay Catalyst

A zirconium-modified montmorillonite clay catalyst is prepared by treatment of Engelhard Clay-24 with an ethanolic (0.5N) solution of zirconium(IV) chloride following the procedures of Example 9.

The zirconium content of the modified clay is analyzed to be 3.8 wt. %.

A 0.1 g of this zirconium-modified clay is then utilized as catalyst for the conversion of cumene hydroperoxide (40 g) to phenol/acetone following the procedures of Example 10.

After 1 hour reaction time.
Estimated cumene hydroperoxide conversion is = 68%
Estimated phenol yield is = 68 mole %
Composition of the product solution after 1 hour is:

| | |
|---|---|
| Acetone | 71.3 wt % |
| Cumene | 2.1 wt % |
| Methyl styrene | 0.4 wt % |
| Phenol | 13.3 wt % |
| 2-phenyl-2-propanol | 2.3 wt % |
| Acetophenone | 0.5 wt % |
| Cumene hydroperoxide | 10.1 wt % |

EXAMPLE 15

Preparation Of Titanium(IV) Chloride Modified Clay

To a 2-liter aqueous solution of titanium(IV) chloride (0.5N, containing 190 g of $TiCl_4$) is added with stirring 200 g of extruded montmorillonite clay (Grade 62, from Engelhard, 1/16" extrudates). Stirring is maintained for 2 days at room temperature.

The extrudates are then recovered by filtration, washed with distilled water, dried in vacuo at 40° C., and sieved through #10 and 20 mesh screens.

Titanium content of the finished extrudates is 2.1 wt. %

EXAMPLE 16

Phenol/Acetone Generation Using Titanium-Modified Clay Catalyst

To a continuous, plug-flow reactor equipped with heating/cooling capabilities is charged 150 cc of the titanium-modified catalyst of Example 15. The catalyst is pretreated with a stream of acetone at 60° C., and then 80% cumene hydroperoxide diluted with an acetone/cumene/phenol mix is passed through the catalyst bed in the up flow mode.

A typical liquid feed composition is as follows:

| | |
|---|---|
| Acetone | 25.3% |
| Cumene | 13.4% |
| Phenol | 37.3% |
| α-Methyl styrene | — |
| Acetophenone | 0.1% |
| 2-Phenyl-2-propanol | 1.6% |
| Cumene hydroperoxide | 22.2% |

Reactor operating conditions are 60°, 300 psi pressure and a total liquid feed rate of 3.3 lbs/hr, i.e. LHSV=10.

The typical product effluent under these conditions comprises:

| | |
|---|---|
| Acetone | 33.8% |
| Cumene | 13.4% |
| Phenol | 50.6% |
| α-Methyl styrene | 0.6% |
| Acetophenone | 0.2% |
| 2-Phenyl-2-propanol | 0.2% |

-continued

| | |
|---|---|
| Cumene hydroperoxide | 0.2% |

Estimated cumene hydroperoxide conversion= >99%
   yield of phenol=97 mole %
   yield of acetone= >99 mole %
The data in Examples 17 through 20 illustrate:
  1 Regeneration of Engelhard Clay, Grade #24, used in phenol/acetone generation, by Soxlet extraction with concentrated nitric acid. The regenerated catalyst (6337-59-1) shows the following in comparison with a control sample of used catalyst, (6337-49-1-1), Example 17:
  a. Improved phenol productivity—see FIG. 9.
  b. Higher levels of cumene hydroperoxide conversion
  c. Higher ash contents—and therefore a lower level of organic contaminants.
  d. Improved color—pale yellow versus yellow-brown-indicative of reduced levels of organic polymer (phenolic resins, etc.)
This regenerated catalyst also shows higher activity in comparison with fresh samples of Clay-24, see FIG. 9.
  2. Regeneration of Engelhard Clay, Grade #25, used in phenol/acetone service by Soxlet extraction with concentrated nitric acid. The regenerated catalyst (6337-96-1-5) again shows (in comparison with a control sample of used catalyst, (6337-84-1-5), Example 18:
  a. Improved phenol productivity—See FIGS. 10 and 11
  b. Higher levels of cumene hydroperoxide conversion
  c. Higher ash contents
  d. Improved color
  3. Regeneration of Engelhard Clay, Grade #25, used in phenol/acetone service by treatment with methanol, particularly at higher temperatures. Once again the regenerated catalysts show as demonstrated by Examples 19 and 20:
  a. Improved phenol productivity—see FIG. 10
  b. Higher levels of cumene hydroperoxide conversion
  c. High ash contents

EXAMPLE 17

A 150 cc sample of Engelhard Clay-24 was subject to 3 days of use as a catalyst for phenol/acetone generation from cumene hydroperoxide. The recovered catalyst comprised brown and yellow granules, sample 6337-49-1-1.

An analysis for ash content of the fresh and used Clay-24 gave the following results.

| | |
|---|---|
| Fresh Clay-24 | 80.7% |
| Used Clay-24 | 68.3% |

An activity test for samples of the new and used Clay-24 catalyst was also conducted as follows:

To a 250 cc round-bottom flask fitted with a condenser, heater, stirrer and feed control, is charged a mixture of 60.0 g of acetone and 0.1 g of Clay-24 catalyst. The mixture is heated to reflux (57° C.) with stirring, and 40.0 g of 80% cumene hydroperoxide solution added dropwise such that the pot temperature does not exceed 66° C. Small samples of the reactant solution (≈2 cc) are withdrawn at regular periods and analyzed by glc.

The composition of the "80%" cumene hydroperoxide feed is:

| | |
|---|---|
| Cumene hydroperoxide | 78.5% |
| Cumene | 16.5% |
| 2-phenyl-2-propanol | 4.7% |
| Acetophenone | 0.4% |

Figure 9:
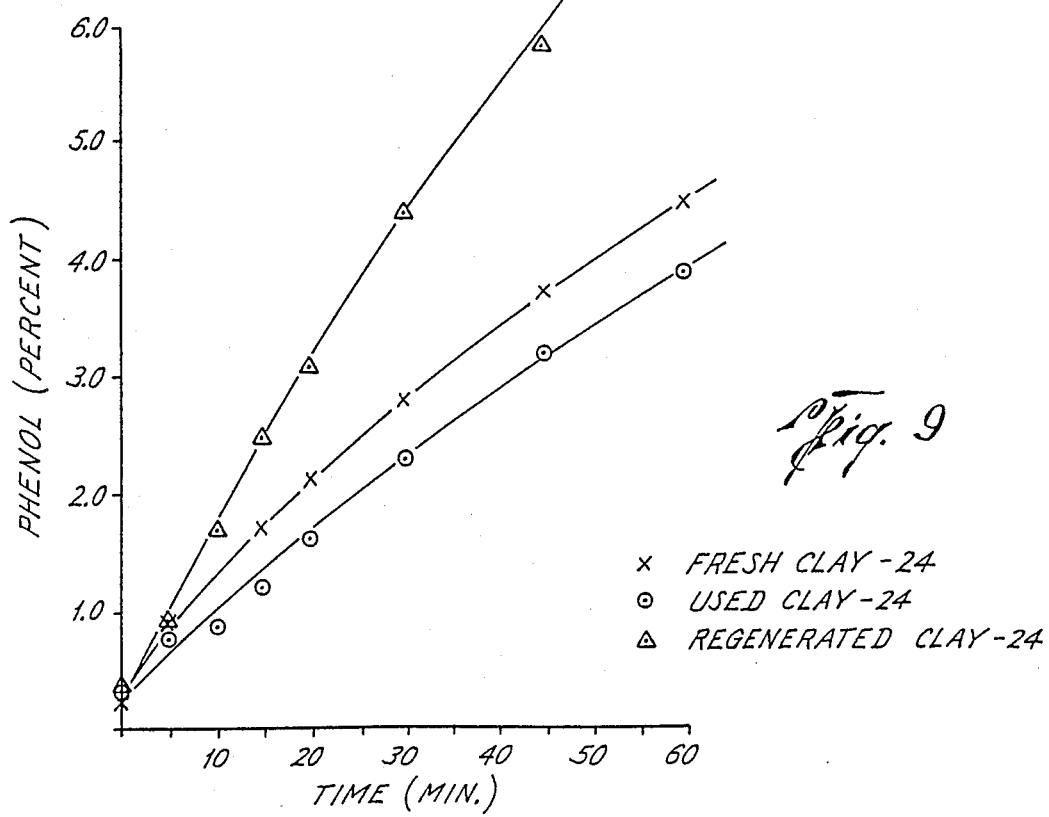

The phenol content of the reactant solution using the new and used Clay-24 catalyst is illustrated in FIG. 9. After 1 hour reaction time:
  For the fresh Clay-24 catalyst:
    Estimated cumene hydroperoxide conversion=24%
    Estimated phenol yield=23 mole %
  Whereas for the used Clay-24 catalyst 6337-49-1-1:
    Estimated cumene hydroperoxide conversion=20%
    Estimated phenol yield=20 mole %

A sample of the used Clay-24 catalyst was then regenerated as described in the following method:

About 20 cc (16.0g) of used Clay-24 (Sample 6337-49-1-1) is placed in a porous ceramic thimble in a Soxlet extractor and extracted with 600 cc of refluxing concentrated nitric acid for a period of 3 hours. After cooling, the solid catalyst is washed with copious amounts of water and acetone, and dried in vacuo. 13.5 g of pale yellow granules were recovered.

An analysis of ash content of the regenerated Clay-24 (Sample 6337-59-1-1) gave the following result—81.6%.

An activity test for the same regenerated Clay-24, conducted as described above, is also shown in FIG. 9. After 1 hour reaction time.
  Estimated cumene hydroperoxide conversion=50%
  Estimated phenol yield is 40 mole %

EXAMPLE 18

A 150 cc sample of Engelhard Clay, Grade 25, was subject to 3 days of use as a catalyst for phenol/acetone generation from cumene hydroperoxide. The recovered catalyst comprised brown and yellow granules, Sample 6337-84-1-5.

An analyses for ash content of the used Clay-25 gave the following result—71.8%.

An activity test for the same sample was also completed as described in Example 17. The phenol content of the reactant solution is illustrated FIG. 10. After 1 hour reaction time (Run 6337-93):
  Estimated cumene hydroperoxide conversion is 19%
  Estimated phenol yield is 13 mole %

A sample (20 cc) of the used Clay-25 catalyst was then regenerated by extraction with concentrated nitric acid as described in Example 17. After cooling, the solid catalyst was washed with water and acetone, and dried in vacuo. 12.6 g of pale yellow granules were recovered.

An analysis of the ash content of the regenerated Clay-25 (Sample 6337-96-1-5) gave the following result—90.6%.

Figure 11:
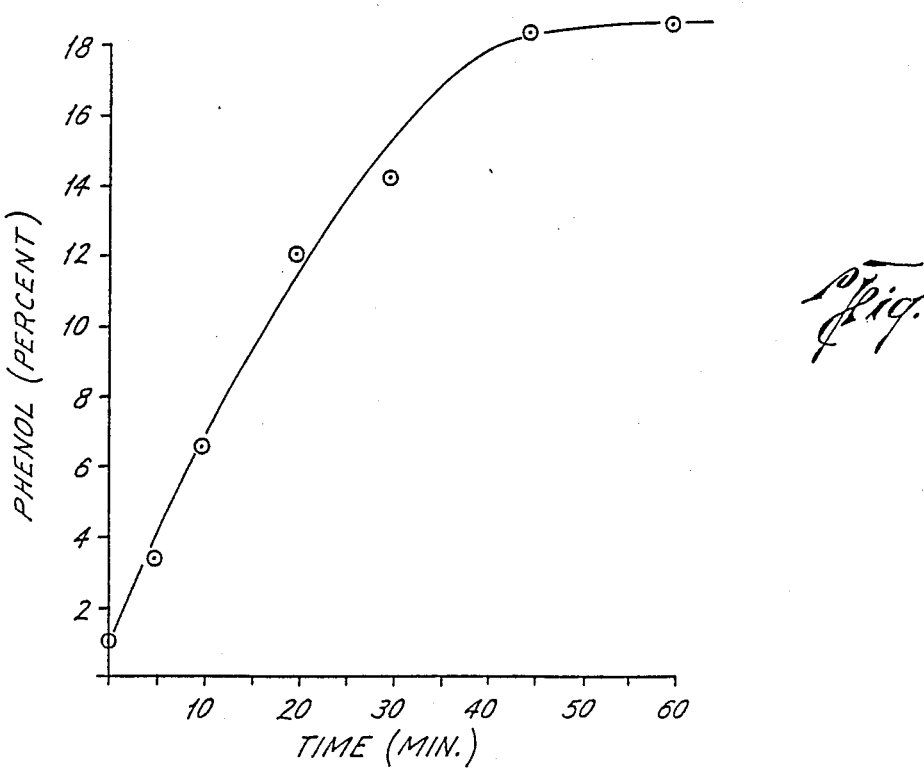

An activity test for the same regenerate Clay-25, conducted as described in Example 17, is shown in FIG. 11. After 1 hour reaction time.

Estimated cumene hydroperoxide conversion = 99%

Estimated phenol yield = 96 mole %

EXAMPLE 19

A sample of the used Engelhard Clay, Grade 25, catalyst of Example 18 was also regenerated by treatment with methanol as described in the following method:

About 30 g of used Clay-25 (Sample 6337-84-1-5) is placed in a round-bottomed flask fitted with a condenser, and refluxed with 100 cc of methanol for 6 hours. On cooling, the remaining solids are recovered by filtration, washed with methanol and dried in vacuo.

An analysis of the ash content of the regenerated Clay-25 (Sample 6337-84-1-reg) gave the following result—92.5%.

Figure 10:
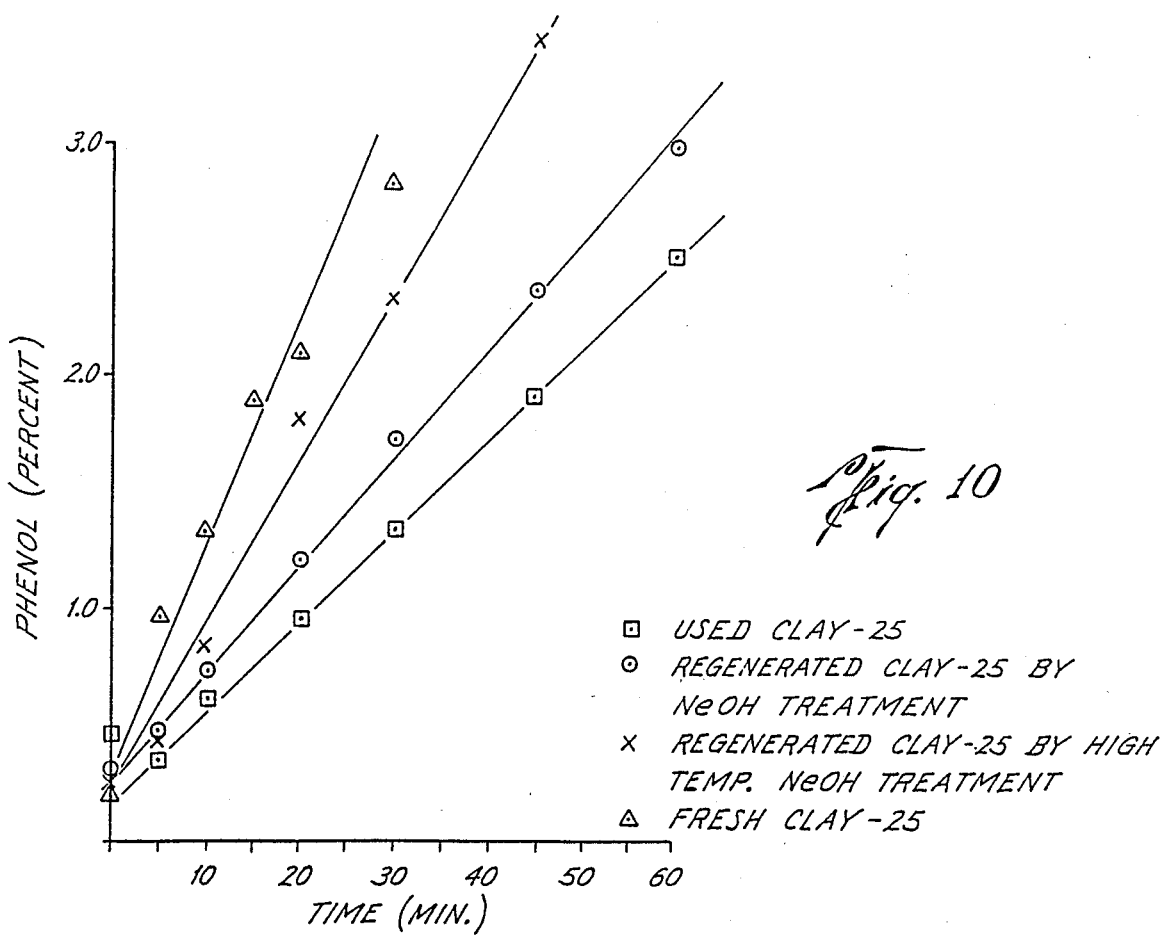

An activity test for the same regenerated Clay-25, conducted as described in Example 17, is shown in FIG. 10. After 1 hour reaction time:

Estimated cumene hydroperoxide conversion = 23%

Estimated phenol yield is 15 mole %

EXAMPLE 20

Another sample of the used Engelhard Clay Grade 25, catalyst of Example 18 was regenerated by treatment with methanol, but this time at higher temperatures in an autoclave, as described in the following method:

About 30 g of used Clay-25 (Sample 6337-84-1-5) is placed in a 300 cc stainless steel autoclave with 100 cc of methanol, and the mixture heated to 150° C., with rocking, for 6 hours. On cooling, the remaining solids are recovered by filtration, washed with methanol, and dried in vacuo.

An analysis of the ash content of the regenerated Clay-25 (Sample 6337-84-2-reg) gave the following result—91.7%.

An activity test for the same regenerated Clay-25, conducted as described in Example 17, is shown in FIG. 10. After 1 hour reaction time:

Estimated cumene hydroperoxide conversion = 41%

Estimated phenol yield = 32 mole %

What is claimed is:

1. In a method for cosynthesis of phenol and acetone by acid-catalyzed decomposition over a catalyst, the improvement comprising reacting cumene hydroperoxide over an acidic montmorillonite clay catalyst which has been modified by the use of a material from the group consisting of heteropoly acids, titanium, zirconium or aluminum at a temperature of about 20° C. to 150° C. and a pressure of from zero to 1000 psig.

2. The method of claim 1 wherein the acidic montmorillonite silica-alumina clay possesses a structure represented by:

$$M_{x/n}{}^{n+} \cdot yH_2O(Al_{4-x}Mg_x)(Si_8)O_{20}(OH)_4$$

where M represents the interlamellar balancing cations from the group consisting of sodium or lithium and x, y and n are integers.

3. The method of claim 1 wherein the montmorillonite clay is modified with a heteropoly acid having the Keggin structure, $H_{8-n}[XM_{12}O_{40}]$ where X = phosphorus or silicon and M = molybdenum or tungsten and n is an integer which is 4 or 5.

4. The method of claim 3 wherein the heteropoly acids are selected from the group consisting of 12-molybdophosphoric, 12-tungstophosphoric, 12-tungstosilicic and 12-molybdosilicic.

5. The method of claim 1 wherein the montmorillonite clay is modified with a compound from the group consisting of zirconium, titanium or aluminum.

6. The method of claim 5 wherein the zirconium, titanium and aluminum are introduced as the salt of an inorganic acid.

7. The method of claim 5 wherein the clay is modified with a compound selected from the group consisting of zirconium(IV) chloride and titanium(IV) chloride.

8. The method of claim 5 wherein the clay is modified with an aluminum compound selected from the group consisting of aluminum nitrate and aluminum(III) chloride.

9. The method of claim 1 wherein the modified acidic montmorillonite clays are in a form from the group consisting of powders, granular forms or extruded forms.

10. The method of claim 1 wherein phenol/acetone are produced continuously and the feed liquid hourly space velocity (LHSV) is between 1 and 10 or greater.

11. The method of claim 1 wherein the temperature is between 40° and 120° C.

12. The method of claim 2 wherein the acidic clay has an acidity in the range of 3 to 15 mg KOH/gm, titrated to a phenolphthalein end point.

13. The method of claim 2 wherein the surface area of the clay is greater than 30 m²/g.

14. The method of claim 13 wherein the surface area of the clay is from 200 m²/g to 1000 m²/g.

15. The method of claim 2 wherein the operating pressure is from zero to 1000 psig.

16. The method of claim 2 wherein the operating pressure is from 100 psig to 400 psig.

17. The method of claim 2 wherein the cumene hydroperoxide feedstock is about 80% pure.

18. The method of claim 2 wherein the cumene hydroperoxide is diluted.

19. The method of claim 18 wherein the diluent is selected from the group consisting of acetone, or a mix of acetone, cumene and phenol.

20. The method of claim 2 wherein there is no significant quantity of mesityl oxide by product formed.

21. The method of claim 2 wherein the montmorillonite silica-alumina clay, after usage in the cosynthesis of phenol and acetone, is regenerated by treatment with nitric acid.

22. The method of claim 2 wherein the montmorillonite silica-alumina clay, after usage in the cosynthesis of phenol and acetone, is regenerated by treatment with methanol.

* * * * *